United States Patent [19]

Haber et al.

[11] Patent Number: 5,292,318
[45] Date of Patent: Mar. 8, 1994

[54] SYRINGE FILLING AND METERING DEVICE FOR PHARMACEUTICAL CONTAINERS

[75] Inventors: Terry M. Haber, Lake Forest; Clark B. Foster, Laguna Niguel, both of Calif.

[73] Assignee: Habley Medical Technology Corporation, Laguna Hills, Calif.

[21] Appl. No.: 42,841

[22] Filed: Apr. 6, 1993

Related U.S. Application Data

[63] Continuation of Ser. No. 741,777, Aug. 7, 1991, abandoned.

[51] Int. Cl.$^5$ .............................................. A61B 19/00
[52] U.S. Cl. ..................................... 604/407; 604/207; 604/415; 141/21; 141/27
[58] Field of Search ........................... 604/82–92, 604/207–211, 416, 905, 407, 415; 141/18, 21, 27, 329, 330

[56] References Cited

U.S. PATENT DOCUMENTS

| | | | |
|---|---|---|---|
| 2,627,857 | 7/1949 | Marcelli | 141/330 |
| 3,321,098 | 5/1967 | Ogle | 604/415 |
| 3,590,889 | 7/1971 | Vannus | 141/18 |
| 3,815,785 | 6/1974 | Gilmont | 604/211 |
| 3,995,630 | 12/1976 | Van de Veerdonk | 604/92 |
| 4,172,457 | 10/1979 | Choksi et al. | 604/416 |
| 4,259,956 | 4/1981 | Ogle | 604/203 |
| 4,338,980 | 7/1982 | Schwebel et al. | 141/18 |
| 4,432,764 | 2/1984 | Lopez | 604/905 |
| 4,516,967 | 5/1985 | Kopfer | 604/87 |
| 5,060,704 | 10/1991 | Rohrbough | 141/330 |

*Primary Examiner*—C. Fred Rosenbaum
*Assistant Examiner*—Mark Bockelman
*Attorney, Agent, or Firm*—Townsend & Townsend Khourie & Crew

[57] ABSTRACT

A syringe filling and metering device (2, 90) for pharmaceutical containers (4) including a variable volume region housing the liquid pharmaceutical (78) and a needle access portion, such as a septum (74) or piston (104), which is pierced by the needle cannula (72) of the syringe (6), such as by mounting the syringe in a syringe carrier (8). An elongate piston stop (58) is held in place by a piston driver (42) to which the syringe carrier is threadably connected. The syringe carrier is screwed into the piston driver to drive the barrel of the cartridge over the piston, thus forcing the contents of the cartridge through the needle cannula and into the syringe. The invention can also be practiced with the needle cannula piercing the piston so that the movement of the piston into the barrel of the container forces the liquid pharmaceutical through the needle cannula and into the syringe.

4 Claims, 6 Drawing Sheets

SYRINGE FILLING AND METERING DEVICE FOR PHARMACEUTICAL CONTAINERS

This is a continuation of application Ser. No. 07/741,777, filed Aug. 7, 1991, now abandoned.

CROSS-REFERENCE TO RELATED APPLICATIONS

This application is related to the following U.S. patent applications: application Ser. No. 07/741,779 for CONTROLLED ACTION SELF-MIXING VIAL now U.S. Pat. No. 5,158,546, and application Ser. No. 07/741,776 for PRECISION SYRINGE-FILLING MECHANISM now U.S. Pat. No. 5,220,948 both filed on the same day as this application; and application Ser. No. 07/615,610, filed Nov. 19, 1990 for Multi-Chamber Vial, the disclosures of which are incorporated by reference.

BACKGROUND OF THE INVENTION

Safe and effective drug therapy by injection depends not only upon accurate diagnosis, but also on efficient and reliable introduction of the medical substance into the subcutaneous cellular tissue without introducing contaminants or ambient air. The applicable drug or pharmaceutical must first be drawn from the resident container or vial into a syringe before injection. The integrity and features of the vial, therefore, are influential over the overall safety of the injection.

Typically, great care must be taken when a needle cannula of a syringe is used in conjunction with a vial containing a pharmaceutical to be administered to the patient. As the pharmaceutical is drawn out of the container via the needle cannula, precautions must be taken to avoid air being drawn into the syringe. In rigid vials, air must be introduced into the container to fill the void created as the liquid pharmaceutical is withdrawn. This volume of air then becomes susceptible to being mixed with the pharmaceutical or being drawn in through the needle cannula and creating air pockets in the syringe barrel. Catastrophic consequences could result if these air pockets are subsequently injected into the patient along with the liquid pharmaceutical. Also, drawing ambient air into the vial can introduce airborne contaminants to the pharmaceutical.

Some patients, or their parents or guardians, must administer pharmaceuticals on a regular basis. Some medications are very expensive and are also very critical as to dose. Therefore, it is important that the amount of the medication aspirated into the syringe for each dose be precise. Since the person administering the pharmaceutical may not be medically trained, obtaining accurate, consistent injections is often difficult.

SUMMARY OF THE INVENTION

The present invention is directed to a device which permits even an untrained person to easily and accurately fill a syringe with the correct dose of a liquid pharmaceutical. The invention is particularly suitable for users who have impaired vision or reduced manual dexterity because clear visual and audible indications are provided as to the dose being drawn into the syringe. Further, the invention permits the withdrawal of a liquid pharmaceutical from a container without the need to introduce air into the container, thus reducing possibility of contamination of the pharmaceutical.

The syringe filling and metering device for pharmaceutical containers is used with containers of the type including a variable volume region housing the liquid pharmaceutical and a needle access portion pierceable by the needle cannula of the syringe. The needle access portion is typically a septum or a pierceable piston. The device includes structure which couples the syringe to the container so that the needle cannula pierces the needle access portion of the container. This is typically accomplished by mounting the syringe in a syringe carrier. An elongate piston stop is held in place by a piston driver to which the syringe carrier is threadably connected. The syringe can be driven toward the septum end of the cartridge by rotating the syringe carrier relative to the piston driver. The elongate piston stop holds the piston in place so that the barrel of the cartridge is driven over the piston, thus forcing the contents of the cartridge through the needle cannula and into the syringe. Therefore, the amount of pharmaceutical aspirated into the syringe can be easily and precisely controlled by controlling the number of full and partial revolutions of the syringe carrier relative to the piston driver. The invention can also be practiced with the needle cannula piercing the piston so that the movement of the needle end of the syringe into the barrel of the container forces the piston down the barrel to force the liquid pharmaceutical through the needle cannula and into the syringe.

One of the primary advantages of the invention, in addition to the ease of use and accuracy, is that one embodiment can be practiced with conventional pharmaceutical cartridges of the type having a septum at one end, a cylindrical barrel and a piston at the other.

Other features and advantages of the invention will appear from the following description in which the preferred embodiments have been set forth in detail in conjunction with the accompanying drawings.

DESCRIPTION OF THE PREFERRED EMBODIMENTS

Figure 1:
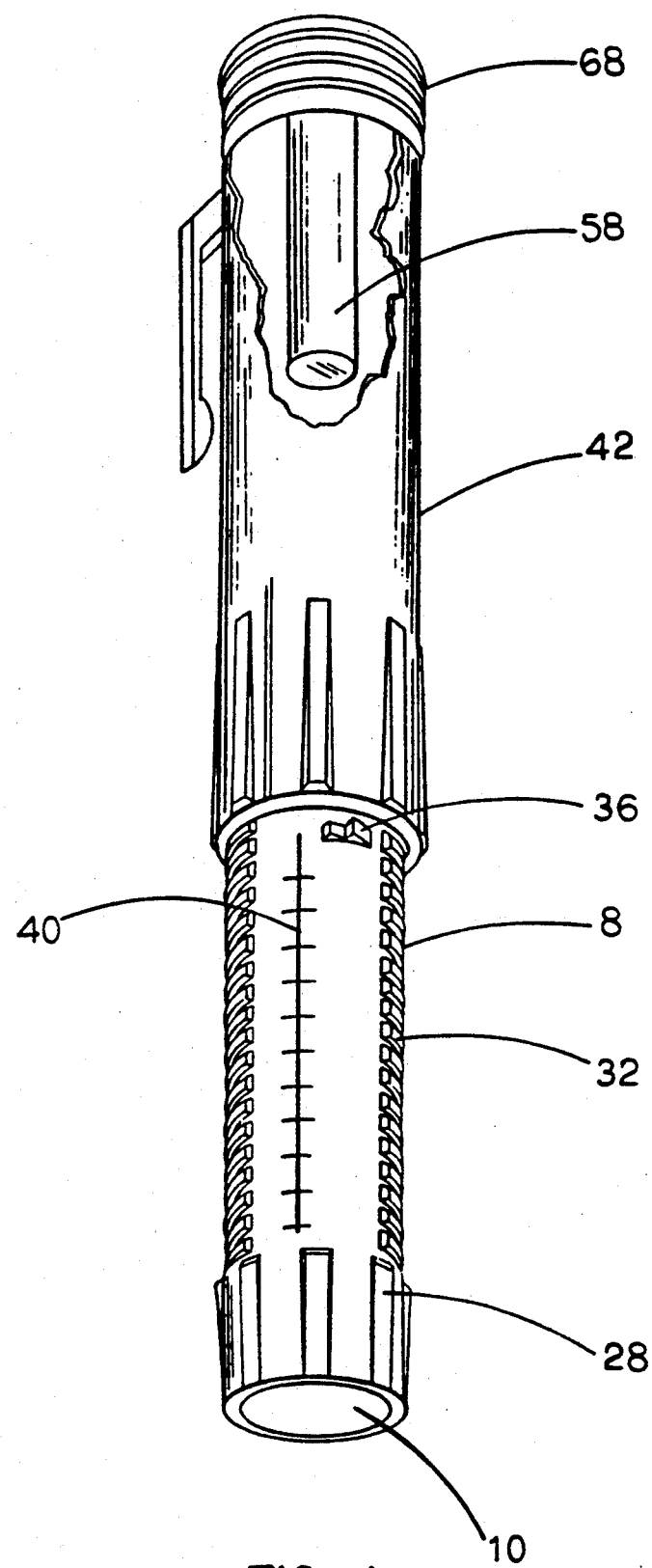
FIG. 1 is an overall isometric view showing a syringe filling and metering device for pharmaceutical containers made according to the invention.
Figure 2:
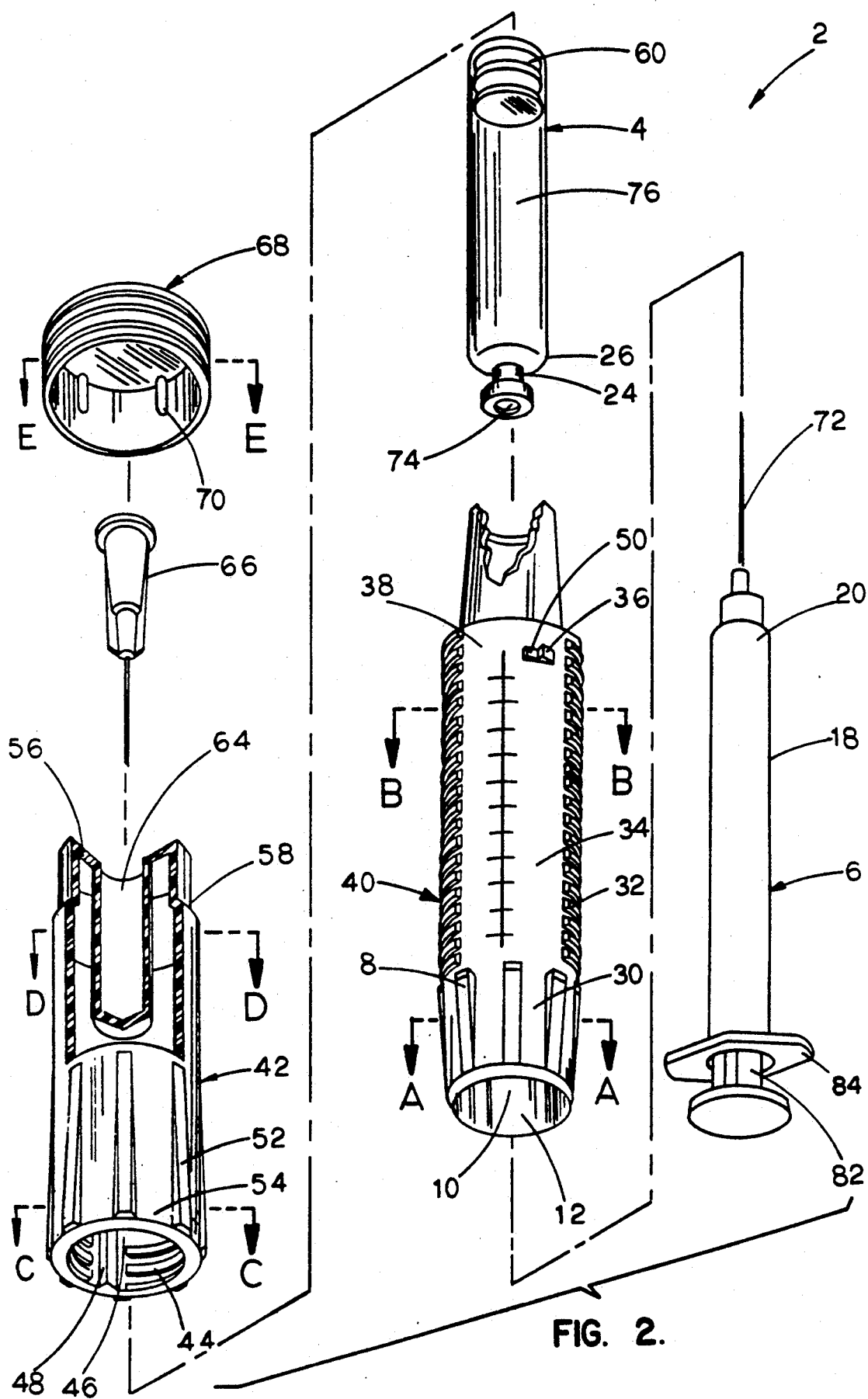
FIG. 2 is an exploded isometric view of the device of FIG. 1 shown with a pharmaceutical cartridge and a syringe.
Figure 2C:
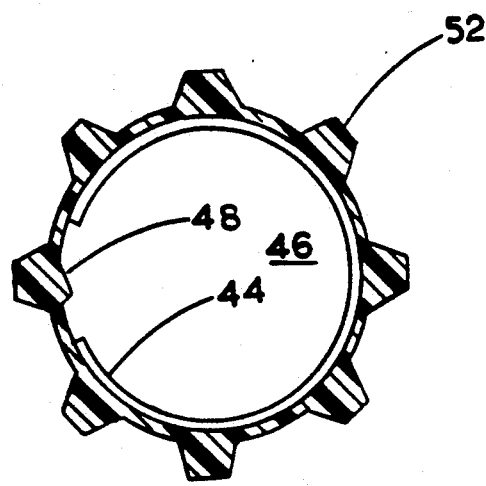
FIGS. 2A-2E are large cross-sectional views taken along lines 2A—2A through 2E—2E of FIG. 2.
Figure 2A:
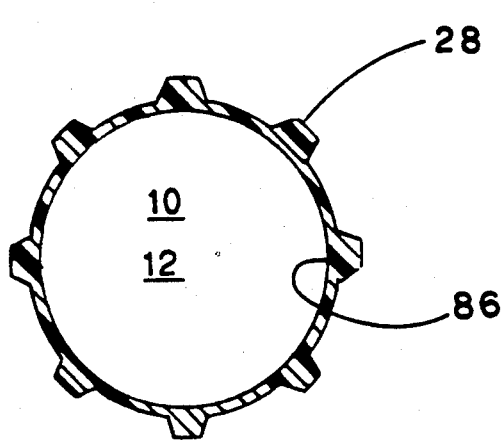
Figure 2D:
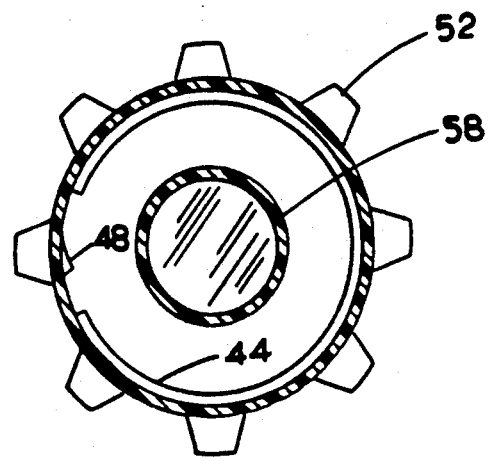
Figure 2B:
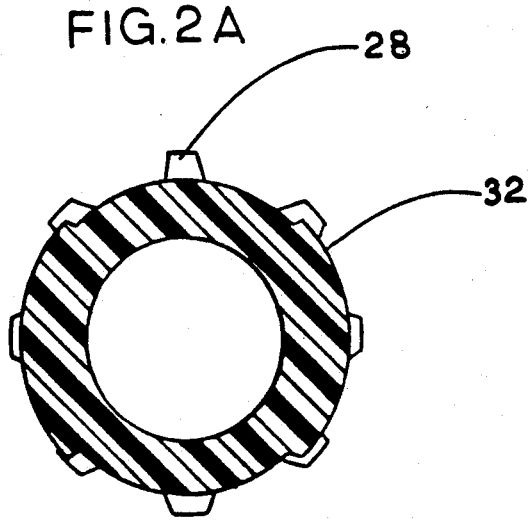
Figure 2E:
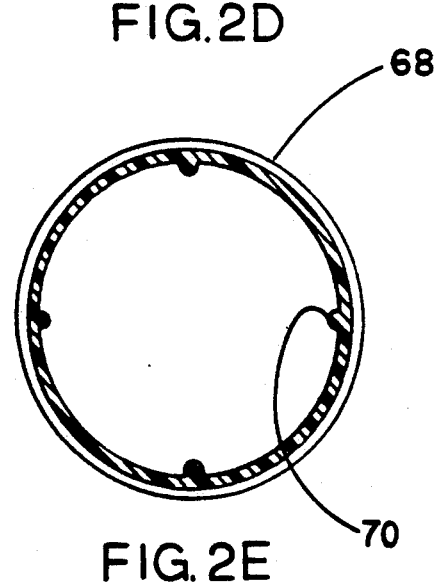
Figures 4, 5:
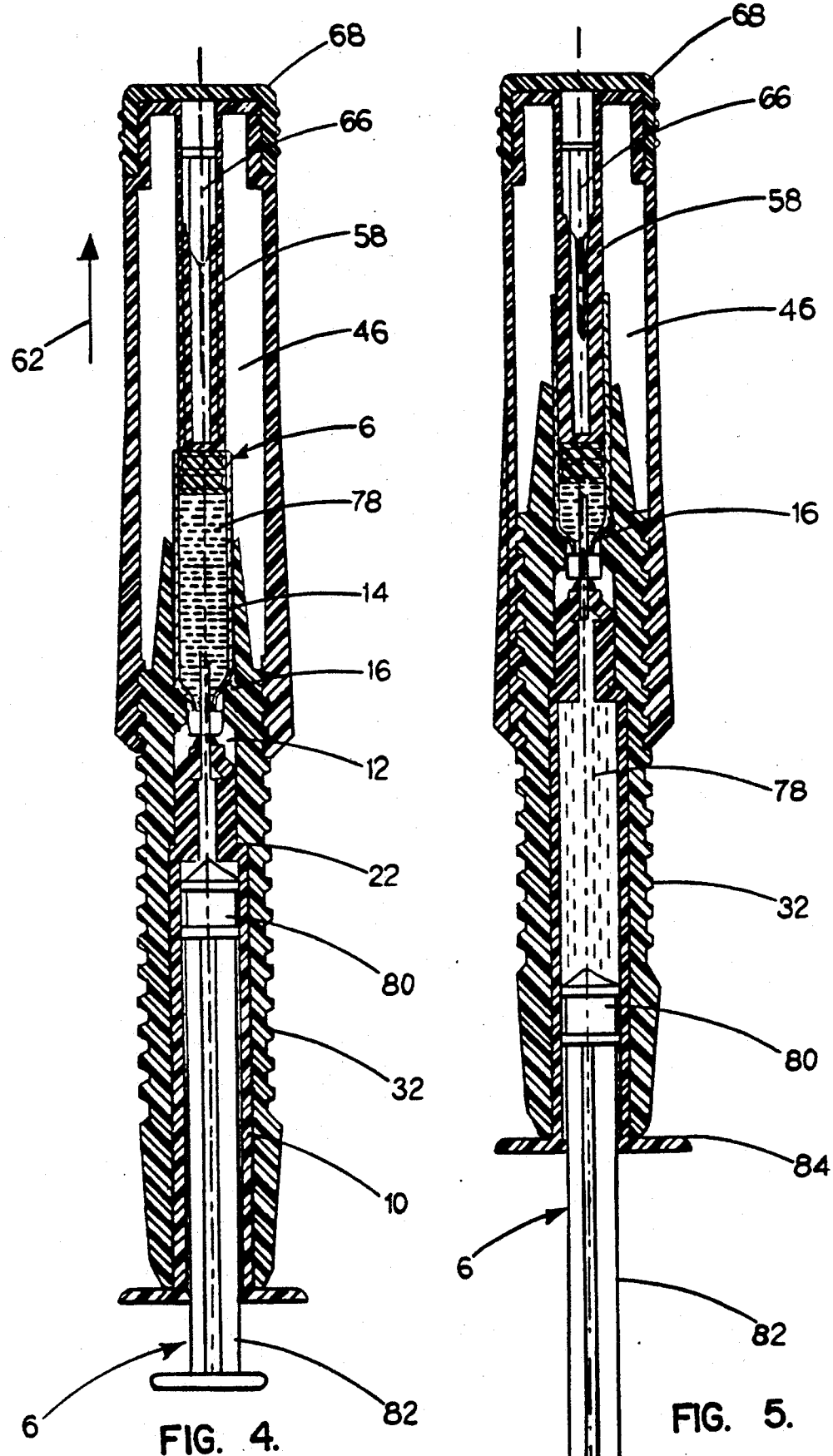
FIG. 4 is a cross-sectional view of the assembly of FIG. 3 shown in the preactuation, post-piercing position.
FIG. 5 shows the assembly of FIG. 4 in the post-actuation, pre-removal condition with a substantial portion of the contents of the cartridge having been forced into the syringe according to the number of turns of the syringe carrier relative to the piston driver.

FIG. 1 illustrates a syringe-filling and metering device 2 specially adapted for use with a conventional pharmaceutical cartridge 4, shown in FIG. 2, and a conventional syringe 6. Device 2 includes a generally tubular syringe carrier 8 having a central bore 10 including a proximal portion 12 and a distal portion 14, seen best in FIGS. 4 and 5, partially separated by an annular ring 16. Proximal portion 12 of central bore 10 is sized so that the barrel 18 of syringe 6 fits snugly within portion 12. The maximum axial movement of syringe 6 into bore 10 is limited by the engagement of a shoulder 20 at one end of barrel 18 with a complementarily positioned shoulder 22 within portion 12 as shown in FIG. 4.

Distal portion 14 of bore 10 is sized to accept cartridge 4. Annular ring 16 is sized and configured to engage a similarly configured ring 24 at the proximal end 26 of cartridge 4. Thus, when cartridge 4 is in the position of FIG. 4, cartridge 4 is snugly retained within distal portion 14 of central bore 10. Syringe carrier 8 also includes a number of axially positioned gripping ridges 28 at the proximal end 30 of syringe carrier 8, threads 32 along the central portion 34 of syringe carrier 8, a detent lock 36 at the distal end 38 of central portion 34 and unit markings 40 along central portion 34. The use of these various elements will be discussed below.

Device 2 also includes a piston driver 42 having internal threads 44 sized to engage external threads 32 as syringe carrier 8 is threaded into the interior 46 of piston driver 42. Piston driver 42 also includes an axially extending detent ridge 48 sized and positioned to engage detent lock 36 each time syringe carrier 8 is rotated once with respect to piston driver 42. Note that detent lock 36 has a central depressed region 50 so that detent ridge 48 can fit within region 50 to temporarily secure syringe carrier 8 and piston driver 42 against relative rotary motion in either direction.

Figure 3:
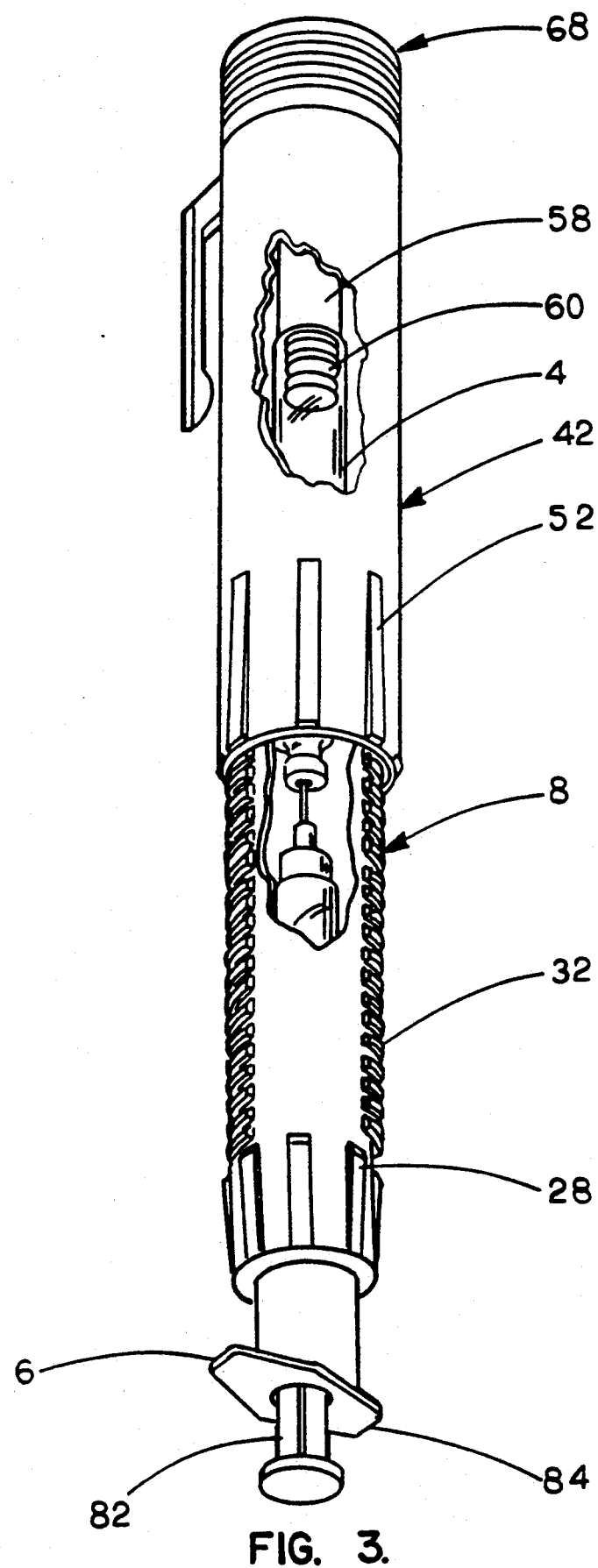
FIG. 3 shows the components of FIG. 2 in an assembled condition with portions broken away to show internal structure.

Piston driver 42 has gripping ridges 52 at its proximal end 54. The distal end 56 is a closed end with an internally extending, generally cylindrical piston stop 58. Piston stop 58, as shown in FIGS. 3 and 4, is positioned to engage a movable piston 60 of cartridge 4 so to keep piston 60 from moving in the direction of arrow 62, that is, towards distal end 56 of piston driver 42. Piston stop 58 has a hollow interior 64 used to house a spare needle assembly 66. A cap 68 is mounted over distal end 56 to cover interior 64 of piston stop 58 and thus keep needle assembly 66 within interior 64. If desired, distal end 56 could be covered with a peel-off sterility film to keep interior 64 clean. Cap 68 has a number of internally extending ridges 70, which help secure cap 68 securely to distal end 56 of piston driver 42.

FIG. 3 illustrates device 2, cartridge 4, and syringe 6 in a preactuation, partially piercing condition with the needle cannula 72 of syringe 6 partially piercing a septum 74 of cartridge 4. Full insertion of syringe 6 into bore 10, with threads 32, 44 engaged to the extent shown in FIG. 4, causes needle cannula 72 to fully pierce septum 74 as shown FIG. 4. The user then grasps syringe carrier 8 and piston driver 42 at gripping ridges 28, 52 and rotates syringe carrier 8 so that it moves into interior 46 of piston driver 42 as shown in FIG. 5. This causes the barrel 76 of cartridge 4 to move over piston stop 58, driving piston 60 along the barrel and thus forcing the liquid pharmaceutical 78 into barrel 18 of syringe 6.

The amount of pharmaceutical delivered into syringe 6 is indicated in several ways. The user can count the number of rotations of syringe carrier 8 within piston driver 42 through the engagement of detent lock 36 with detent ridge 48. This provides both a tactile and audible indication of the amount of pharmaceutical 78 being delivered into syringe 6. The distance syringe carrier 8 moves into piston driver 42 is indicated by unit markings 40 as they pass into interior 46 of piston driver 42. Further, since syringe carrier 8 and piston driver 42 are preferably made from clear materials, such as polycarbonate or acrylic, this permits the movement of piston 60 within cartridge 4 and the movement of piston 80 at the end of stem 82 to be viewed. After the appropriate dose has been provided to syringe 6, the syringe is removed from central bore 10 of syringe carrier 8 using finger grips 84 and the injection is given.

Figure 6:
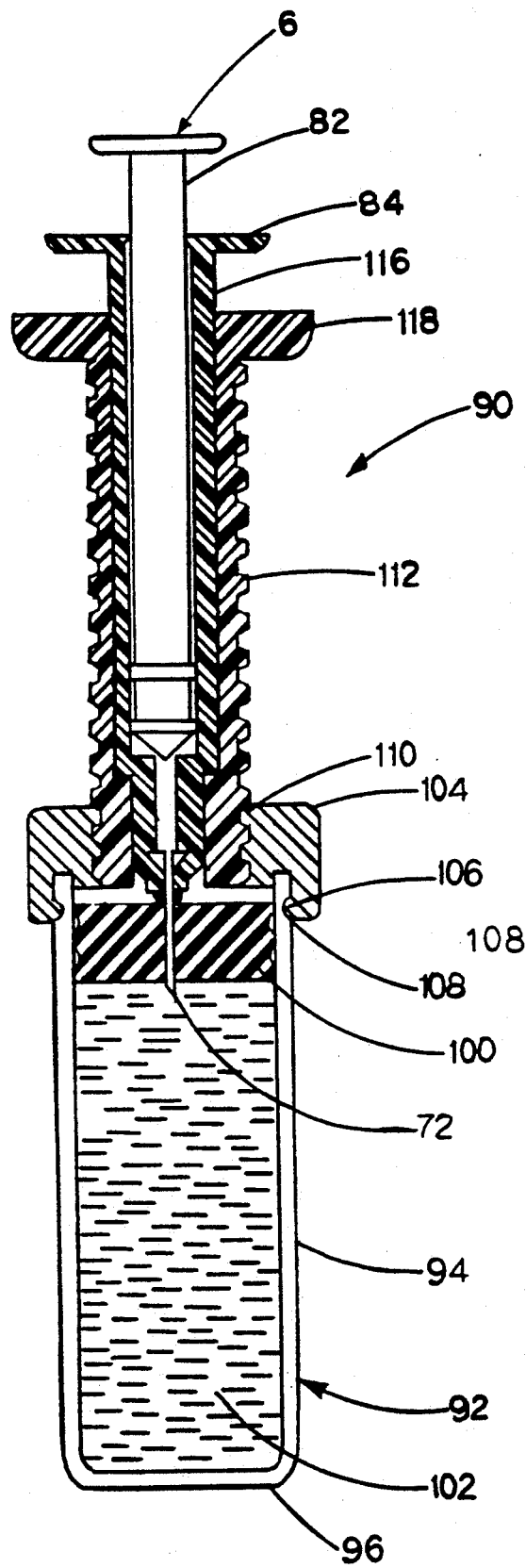
FIG. 6 is a cross-sectional view of an alternative embodiment of the invention shown in the preactuation, post-piercing condition.
Figure 7:
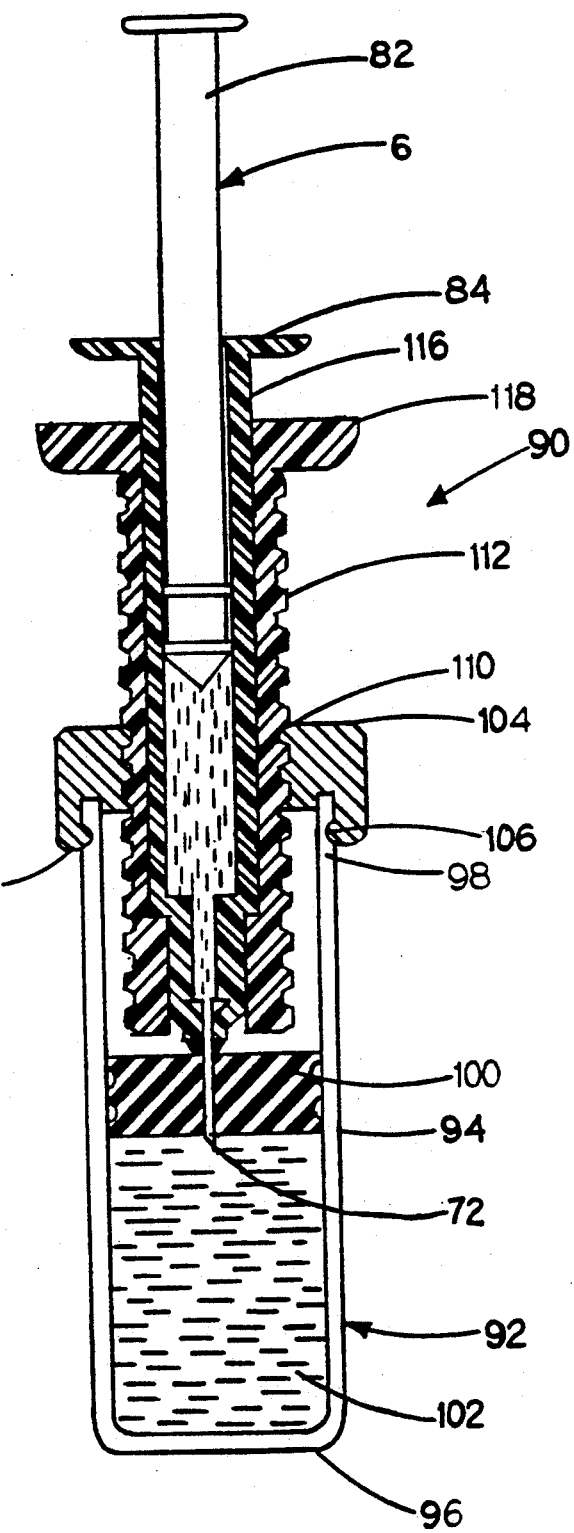
FIG. 7 shows the assembly of FIG. 6 in a post-actuation, pre-removal condition with a portion of the contents of the vial forced into the syringe.

FIGS. 6 and 7 illustrate an alternate embodiment of the invention. These figures illustrate a syringe filling and metering device 90 in combination with syringe 6 and a vial 92. Vial 92 typically includes a glass, cup-shaped container 94 having a closed distal end 96 and an open proximal end 98. Container 94 houses a pierceable, elastomeric piston 100 and contains a liquid pharmaceutical 102 between piston 100 and end 96. Device 90 includes an adaptor ring 104 having an internal bead 106 which engages a like groove 108 at proximal end 98 of container 94. Ring 104 has internal threads 110 which engage the external threads 112 of syringe carrier 114. Syringe carrier 114, like syringe carrier 8, has a central bore 116 sized to snugly hold syringe 6 therein. With syringe carrier 114 threadably engaged to ring 104, syringe 6 is fully inserted into bore 116 to permit needle cannula 72 to pierce piston 100 as shown in FIG. 6. To provide syringe 6 with the appropriate dose of pharmaceutical 102, user grasps ring 104 with one hand and the enlarged proximal end 118 of syringe carrier 114 with the other hand and rotates the syringe carrier to drive the syringe carrier into the interior of container 94. Doing so causes liquid pharmaceutical 102 to be driven up through needle cannula 72 and into barrel 18 of syringe 6. Appropriate dose markings and detent features can be used with device 90 if desired.

Other modifications and variations can be made to disclose embodiments without departing from the subject invention as defined in the following claims. For example, vial 92 could include a pierceable septum at distal end 96.

What is claimed is:

1. A syringe filling and metering device for use with a syringe, of the type including a needle cannula, the device comprising:

a pharmaceutical container including a generally cylindrical body with an open end and a closed end, a movable piston within the body and a liquid housed within a variable volume region defined between the piston and the closed end, the piston being pierceable by the needle cannula;

an open ended syringe carrier to which the syringe is mounted, the syringe carrier having a distal end with external threads;

the open end of the pharmaceutical container having an inner surface and internal threads formed on said inner surface, said internal threads mating to the external threads of the syringe carrier so to mount the syringe carrier therewith to the pharmaceutical container with the needle cannula piercing the piston;

the syringe carrier being sized to enter through the open end of the pharmaceutical container and exert a force upon the piston thereby driving the piston towards the closed end so as to force the liquid through the needle cannula and into the syringe when the syringe carrier and pharmaceutical container are rotated with respect to one another; and means for precisely indicating the volume of liquid which has been transferred from the pharmaceutical container to the syringe wherein said indicating means includes a detent lock protruding from an outer surface of the syringe carrier and a detent ridge axially extending along the inner surface of the pharmaceutical container, the detent ridge sized and positioned to engage the detent lock each time the syringe carrier is rotated a set distance with respect to the pharmaceutical container.

2. The device as claimed in claim 1 wherein the pharmaceutical container is made of clear glass to provide visual indication of the transfer of the liquid from the pharmaceutical container to the syringe.

3. A syringe filling and metering assembly comprising:

a piston driver having an inner surface and internal threads formed on said inner surface;

an elongate piston stop housed within the piston driver;

a pharmaceutical cartridge, including a hollow body with first and second ends, a needle-pierceable septum at the first end, a piston slidably mounted within the body between the first and second ends, the second end being open and through which the piston stop passes to engage the piston, the pharmaceutical cartridge including a liquid within a variable volume region defined between the piston and the septum;

an open ended syringe carrier to which a syringe with a needle cannula is mounted, the syringe carrier including external threads mating to the internal threads of the piston driver so to mount the syringe carrier and syringe therewith to the piston driver, with the needle cannula piercing the septum of the pharmaceutical cartridge;

whereby rotating the external threads with respect to the internal threads causes the piston stop to force the piston towards the septum so as to force the liquid through the needle cannula and into the syringe; and means for precisely indicating the volume of liquid which has been transferred from the pharmaceutical cartridge to the syringe said indicating means including a detent lock protruding from an outer surface of the syringe carrier and a detent ridge axially extending along the inner surface of the piston driver, the detent ridge sized and positioned to engage the detent lock each time the syringe carrier is rotated a set distance with respect to the piston driver.

4. The device as claimed in claim 3 wherein the indicating means includes unit markings on an outer surface of the syringe carrier.

* * * * *